United States Patent [19]

Aston et al.

[11] Patent Number: 5,395,507
[45] Date of Patent: Mar. 7, 1995

[54] ELECTROCHEMICAL GAS SENSOR

[76] Inventors: William J. Aston, Little Kents Oak, Awbridge, Hampshire, SO51 OHH; Yat S. Chan, 5 Dulwich Wood Park, London SE19 1QX, both of United Kingdom

[21] Appl. No.: 154,136

[22] Filed: Nov. 17, 1993

[30] Foreign Application Priority Data

Dec. 24, 1992 [GB] United Kingdom ................ 9226937

[51] Int. Cl.6 ............................................. G01N 27/26
[52] U.S. Cl. .................................. 204/431; 204/432; 204/412; 204/415; 422/98
[58] Field of Search ............... 204/431, 432, 412, 415, 204/424, 425, 426, 427; 422/98

[56] References Cited

U.S. PATENT DOCUMENTS

| | | | |
|---|---|---|---|
| 3,992,267 | 11/1976 | Oswin et al. | 204/431 |
| 4,118,194 | 10/1978 | Raleigh | 422/98 |
| 4,221,651 | 9/1980 | Mansfield | 204/195 |
| 4,406,770 | 9/1983 | Chan et al. | 204/432 |
| 5,173,166 | 12/1992 | Tomantschger | 204/412 |
| 5,242,765 | 9/1993 | Naimer et al. | 429/42 |

Primary Examiner—John Niebling
Assistant Examiner—Bruce F. Bell
Attorney, Agent, or Firm—Lee, Mann, Smith, McWilliams, Sweeney & Ohlson

[57] ABSTRACT

An electrochemical gas sensor comprises sensing and counter electrodes (1,2). A conduit (15) permits access of gas to the sensing electrode (1). An electrolyte reservoir (23). A porous, block-like body (24) is positioned in the reservoir (23) for conveying electrolyte to the sensing and counter electrodes and at least partly supporting other components of the sensor.

15 Claims, 2 Drawing Sheets

ELECTROCHEMICAL GAS SENSOR

FIELD OF THE INVENTION

The invention relates to electrochemical gas sensors of the kind comprising sensing and counter electrodes, means for permitting access of gas to the sensing electrode; an electrolyte reservoir; and means for conveying electrolyte to the sensing and counter electrodes. Such electrochemical gas sensors are hereinafter referred to as of the kind described.

DESCRIPTION OF THE PRIOR ART

An example of an electrochemical gas sensor of the kind described is shown in GB-A-2094005. In this case the reservoir is provided in a hollowed out bottom plate which has a covering flange which supports the various components of the sensor including the sensing and counter electrodes and, where provided, a reference electrode. Electrolyte passes through a small aperture in the covering flange in a wick extending into the reservoir and extending through apertures in some of the components and into contact with hydrophylic separators to convey electrolyte to the region between the sensing and counter electrodes. The use of a wick is undesirable due to the complex manufacturing techniques required to thread the wick through the various components. Furthermore, the arrangement requires an additional rear vent which provides a possible source of leakage as well as leading to a more complex construction.

SUMMARY OF THE INVENTION

In accordance with one aspect of the present invention, an electrochemical gas sensor of the kind described is characterised in that the conveying means includes a porous, block-like body positioned in the reservoir and at least partly supporting other components of the sensor. The term "block-like" is intended to mean any 3-dimensional shape which provides a supporting surface for the other sensor components.

We have devised a much simpler sensor construction in which the reservoir includes a porous, block-like body which not only provides the conveying means but also at least partly supports other components such as electrodes, separators and the like of the sensor.

Preferably, the porous, block-like body only partly fills the reservoir. With this arrangement, there will be some free space within the reservoir which can balance pressure differentials between the region inside the sensor and ambient pressure by venting forwards and thus avoiding the need for a rear vent. The free space is also necessary to allow water uptake during exposure to high relative humidities and expansion during temperature changes. To that end, the block-like body preferably has a substantially square cross-section while the reservoir has a substantially circular cross-section.

Preferably, the porous, block-like body is at least partially hydrophobic. This is particularly advantageous during assembly of a sensor since the sensor can be assembled by first supplying electrolyte to the reservoir; placing the porous, block-like body in the reservoir (and electrolyte); assembling the remaining components and sealing the resulting assembly. Thereafter, the assembly can be inverted to cause the electrolyte to wet through to the sensing and counter electrodes. This should be contrasted with the conventional method which requires that the components are assembled in dry form, the assembly sealed, and then electrolyte supplied through a side opening which has to be subsequently plugged and sealed.

The porous, block-like body can be electrically conducting or non-conducting and could be constituted, for example by VYON, a porous, high density, polyethylene made by Porvair plc of Kings Lynn, Norfolk, England. VYON is also partially hydrophobic. Preferably, however, the body is electrically conductive and electrochemically active since in that case the body can also form the counter-electrode. This simplifies still further the construction of the device. This is particularly useful where the reaction involved is either oxygen reduction or evolution, ie. where the sensing electrode reaction is either anodic oxidation (as in a CO sensor) or a cathodic reduction (as in a chlorine sensor) respectively.

If additional catalytic activity is required, an additional, counter-electrode member can be arranged to contact the electrically conducting and electrochemically active body. The body then acts as both a current collector aid (although a separate current collector would also be necessary) and as an additional surface for the counter electrode reaction. Alternatively, or in addition, active electro-catalyst (for example Pt-black) can be deposited in the pores of the body (eg VYON) to provide a more active electro-catalytic electrode.

The preferred material for use as the block-like body is Reticulated Vitreous Carbon (RVC). This material is manufactured by The Electrosynthesis Co Inc., P.O. Box 16, East Amhurst, N.Y. 14051, U.S.A. RVC is an open pore "foam" material composed solely of vitreous carbon which is a glass-like carbon combining some of the properties of glass with some of those of normal industrial carbons. RVC has an exceptionally high void volume (97%), high surface area combined with self-supporting rigidity, low resistance to fluid flow, electrical conductivity, and electro-chemical activity. Furthermore, it has exceptional chemical inertness over a wide temperature range, being particularly compatible with strong mineral acid electrolytes. It is very light (low density) and easily formed and handled into the desired shapes for these applications.

In accordance with a second aspect of the present invention, an electro-catalytic gas electrode includes an electrically conductive and electrochemically active porous member whose pores are impregnated with an electrocatalyst.

This new electrode should be contrasted with conventional electrodes of pressed catalyst/PTFE mixtures directly onto porous PTFE tape, with the metal foil current collectors providing a simple pressure contact of the catalyst layer. The new electrode is particularly useful in an electrochemical gas sensor in that it enables one member of the sensor construction, namely the reference or counter electrode, to be eliminated.

Preferably, the electrode is made from RVC.

The electrode could comprise a reference electrode or a counter electrode.

BRIEF DESCRIPTION OF THE DRAWINGS

Some examples of gas sensors and electrodes according to the invention will now be described and contrasted with a known example with reference to the accompanying drawings in which.

DETAILED DESCRIPTION OF EMBODIMENTS

Figure 1:
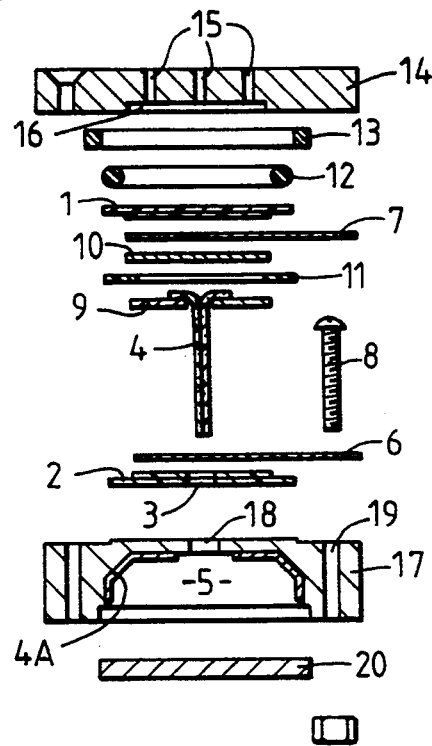
FIG. 1 is an exploded, sectional view through a conventional gas sensor.

The conventional sensor shown in FIG. 1 is more fully described in GB-A-2094005, the contents of which are incorporated herein by reference. It should be noted that the drawings are not to scale.

Referring to FIG. 1, a sensing electrode 1 comprises porous PTFE tape to which is bonded a catalyst/PTFE mixture, the latter covering an area of smaller diameter than the tape. A counter electrode 2 is of similar construction but with a hole 3 through which a wick 4 passes to an electrolyte reservoir/expansion chamber 5. Strip-like current collectors 6, 7 contact the sensing and counter electrodes respectively (see also FIG. 2) and lead out to terminal posts 8 (one only shown). The wick 4 extends from a separator 9 which with a further separator 10 and an annular gasket 11, which gasket may conveniently be cut from porous PTFE tape, makes up an interior sandwich between the electrodes.

Above the sensing electrode 1 is an O-ring 12 with a rigid retaining ring 13 of smaller height than the O-ring, the underside of which has slots (not shown) to allow egress of the current collectors 6 and 7. A top plate 14 carries capillary holes 15 which form a diffusion barrier for restricting access of the gas to be detected and has a cavity 16 to allow for diffusion across the sensing electrode. A bottom plate 17 carries the electrolyte reservoir/expansion chamber 5. The wick 4 passes through a hole 18 therein, and is arranged to make good contact with wick extension 4a which extends around the perimeter of chamber 5 to ensure contact with the electrolyte in all sensor attitudes. The reservoir is closed by a cover plate 20. It will be noted that the wick is necessary since the floor of the base plate supports the electrode stack and electrolyte must therefore wick through the small hole 18 in the centre of the base plate.

After assembly the whole is sealed or clamped together, for example with bolts and nuts (not shown) through the top and bottom plates 14 and 17, ultrasonic welding, thermal welding, or crimp methods. The O-ring is thereby compressed. The outer annular portions of the PTFE tape in the electrodes 1 and 2, not covered with catalyst, are thus brought into intimate compressive contact with the PTFE gasket 11. The PTFE moulds around the current collectors leading out of the cell from the electrodes.

With the assembly on its side, electrolyte may now be introduced to partially fill the reservoir 5 via a side aperture (not shown) in bottom plate 17 which is then plugged using a plastic plug and suitable cement. The electrolyte wets up the separators 9 and 10 via the wick 4 to form the electrolyte connection between the electrodes. The amount of electrolyte is chosen to only partially fill the reservoir/expansion chamber 5 and so that volume changes resulting from gain or loss of water vapour during the operation of the sensor may be accommodated. An air vent (not shown) is provided in a cover plate 20 to accommodate expansion/contraction within the reservoir 5.

Operation of the sensor is described in detail in GB-A-2094005.

Figure 2:
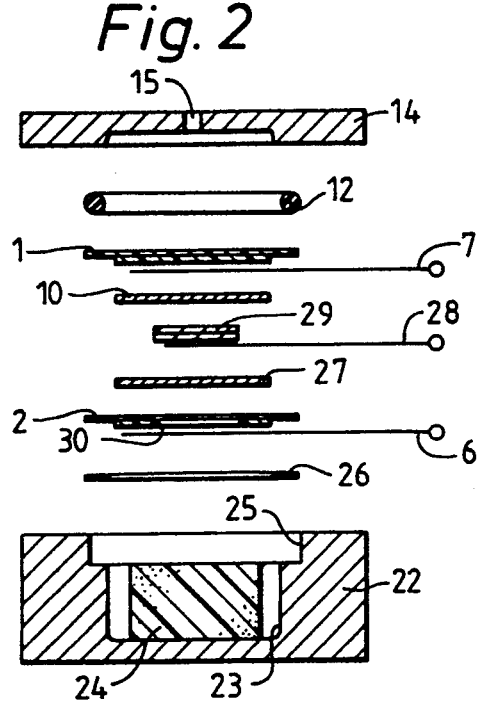
FIG. 2 is an exploded, sectional view through an example of a sensor according to the invention.

As explained above, the construction of the reservoir involving the cup wick 4A and the main wick 4 is complex leading to expense in manufacture as is the method of assembly. FIG. 2 is a view similar to FIG. 1 but showing an example of a gas sensor according to the invention. In this drawing, items corresponding to items shown in FIG. 1 have been given the same reference numerals. In this case, however, the sensor is a three electrode sensor rather than a two electrode sensor.

Figure 3:
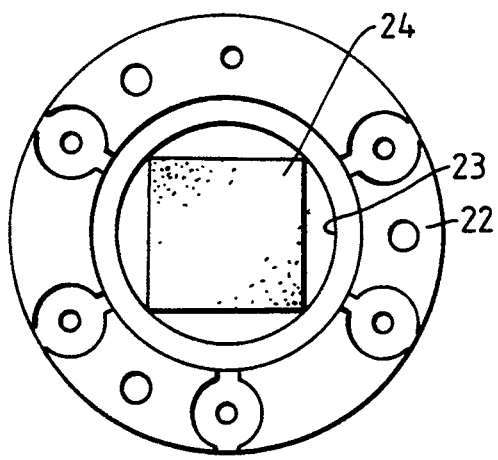
FIG. 3 is a plan view of the base plate/reservoir of the FIG. 2 example.

The base plate 22 has a reservoir or well 23 opening upwardly and facing towards the electrodes. A plug of RVC or Vyon material 24 having a substantially square cross section (FIG. 3) sits in the reservoir 23 with a top surface substantially flush with a widened bore 25 in the base plate 22.

Supported above the plug 24 and partially by the plug and partially by the floor of the widened bore 25 are positioned a PTFE tape floor seal 26, the current collector 6 and counter electrode 2, a separator 27 of hydrophylic material, a current collector 28, a reference electrode 29, the separator 10, the current collector 7 and the sensing electrode 1. The components are held in place as before by sealing the top plate 14 onto the base plate 22, the various components being urged into-contact by the O-ring 12.

When assembled, the separator 27 will contact the plug 24 through an aperture 30 in the counter electrode 2 and electrolyte can pass from the plug 24 through the separator 27 into the region of the reference electrode 29 and through the separator 10 into the region of the sensing electrode 1. At the start of an assembly process, electrolyte is supplied to the reservoir 23 following which the plug 24 is positioned in the reservoir. The remaining components shown in FIG. 2 are then assembled with the base plate 22 and are sealed together using any of the methods mentioned above. Following assembly, the assembled device is inverted to allow electrolyte to wet via the plug 24 through the separators. It should be noted that the counter electrode 2 and the floor seal 26 are very thin so that electrolyte will pass easily through from the plug 24 to the separator 27 without the need for a wick. It will also be noted that in contrast to the conventional case, electrolyte is supplied to the reservoir 23 at the beginning of the assembly operation.

The use of a square plug 24 allows internal free space to balance pressure differentials with ambient by venting forward through the floor seal and electrode tapes which are porous but being hydrophobic, do not allow passage of electrolyte. Thus the rear vent of the standard design can be dispensed with.

The free space is necessary to allow water uptake during exposure to high relative humidities and expansion during temperature changes. Pressurising the air in this space must be avoided as the hydraulic pressure built up in the electrolyte will cause leakage through the current collector's outlets.

The electrodes 1, 29, 2 shown in FIG. 2 can be constructed in a conventional manner. However, the electrodes could also be formed from the RVC material as described above.

Not only could the electrodes shown in FIG. 2 be made of the RVC material, but the RVC block itself can be used to constitute one or both of the reference and counter electrodes.

Figure 4:
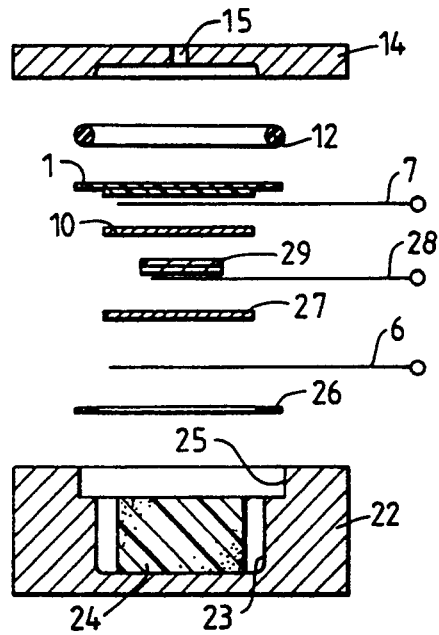
FIG. 4 is a view similar to FIG. 2 but showing a second example.

In a modified example, use can be made of the fact that, unlike the conventional separator material used for wicks, RVC is electrically conducting and electrochemically active. For example, it can support the oxygen reduction reaction. Consequently, it can be used as a combined wick and electrode with the result that the counter electrode 2 can be omitted as a separate item and incorporated into the plug 24. This is shown in FIG. 4 which illustrates an example in which the RVC block 24 constitutes the counter electrode. The floor seal 26 is sufficiently thin for the current collector 6 to make electrical contact with the block 24.

Furthermore, either when it acts as a counter electrode or in association with a separate counter electrode, the Vyon or RVC plug can be arranged to provide extra catalytic activity if its pores are impregnated with catalyst such as silver, gold, platinum or chemically modified materials as used in bioelectrochemical or enzyme electrodes. Alternatively, active electrode materials could be incorporated into the structure to provide an alternative counter or reference electrode action, eg. Ag/AgCl, Ag/Ag$_2$O, PbO$_2$ as examples of cathode active materials or metals such as lead or zinc as examples of anode active materials.

Figure 5:
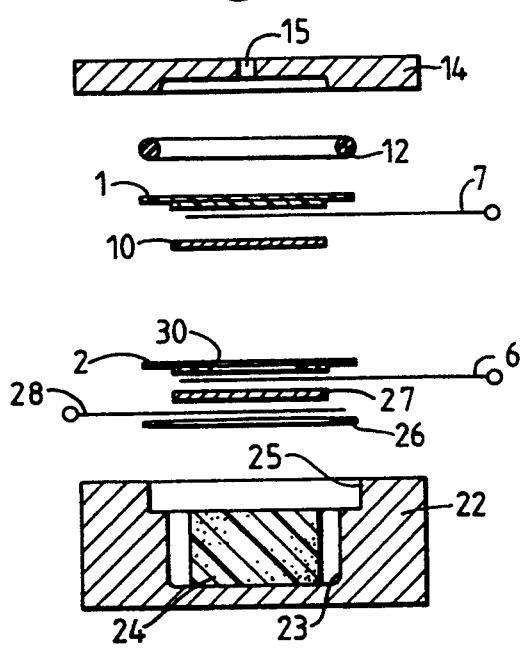
FIG. 5 is a view similar to FIG. 2 but showing a third example.

FIG. 5 illustrates an example in which the RVC block 24 constitutes the reference electrode. In this case, the current collector 28 has been moved to just above the floor seal 26 so that it will make electrical contact with the plug 24 and the separator 27 has been moved between the current collectors 6, 28.

Figure 7:
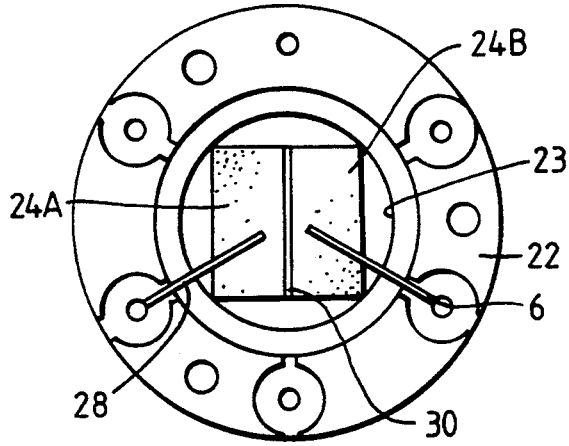
FIG. 7 is a plan of part of the FIG. 6 example.
Figure 6:
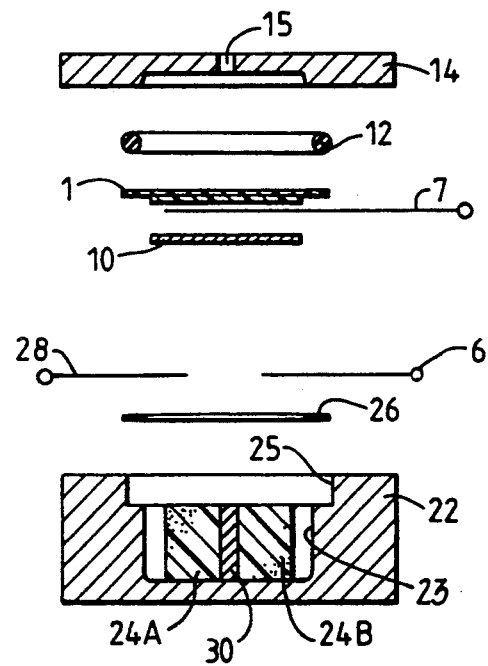
FIG. 6 is a view similar to FIG. 2 but showing a fourth example.

In other examples, the RVC block 24 could provide both the counter and reference electrodes. In some cases, these may be positioned one above the other but in the preferred arrangement, as shown in FIGS. 6 and 7, the RVC block is divided into two portions 24A, 24B which are electrically isolated by an insulator 30. As can be seen most clearly in FIG. 7, the current collectors 6, 28 extend at about 120° to each other over their respective portions of the block 24B, 24A which they will electrically engage when the sensor is assembled.

We claim:

1. An electrochemical gas sensor comprising sensing and counter electrodes and at least one separator between said sensing and counter electrodes, means for permitting access of gas to said sensing electrode; an electrolyte reservoir; and means for conveying electrolyte to said sensing and counter electrodes wherein said conveying means includes a porous, self-supporting body positioned in said reservoir and at least partly supporting said at least one separator.

2. A sensor according to claim 1, wherein said porous, self-supporting body only partly fills said reservoir.

3. A sensor according to claim 1, wherein said porous, self-supporting body is electrically conductive and electrochemically active and forms said counter electrode.

4. A sensor according to claim 3, wherein said porous, self-supporting body incorporates an active electro-catalyst within its pores.

5. A sensor according to claim 1, wherein said porous, self-supporting body is electrically conductive and electrochemically active and forms a reference electrode.

6. A sensor according to claim 1, wherein said porous, self-supporting body is electrically conductive and electrochemically active and is divided into two electrically isolated sections, one constituting said counter electrode and the other constituting a reference electrode.

7. A sensor according to claim 1, wherein said porous, self-supporting body comprises reticulated vitreous carbon.

8. A sensor according to claim 1, wherein said self-supporting body supports said at least one separator and said sensing electrode.

9. A sensor according to claim 8, wherein said self-supporting porous body supports said separator, said sensing electrode, and said counter-electrode.

10. A sensor according to claim 9, further comprising a reference electrode, said porous, self-supporting body also supporting said reference electrode.

11. An electro-catalytic gas electrode including an electrically conductive and electrochemically active porous member whose pores are impregnated with an electrocatalyst, said porous member comprising reticulated vitreous carbon.

12. An electrode used as a counter electrode or a reference electrode or both for an electrochemical gas sensor including an electrically conductive and electrochemically active porous member whose pores are impregnated with an electrocatalyst, wherein said porous member comprises reticulated vitreous carbon.

13. A method of assembling an electrochemical gas sensor comprising positioning a porous self-supporting body in a reservoir; positioning remaining components of the sensor including at least a separator and a sensing electrode above said porous, self-supporting body wherein said porous, self-supporting body at least partly supports said separator; supplying electrolyte to said reservoir; assembling and sealing the remaining components together; and inverting said sensor to allow electrolyte to wet through to said sensing electrode.

14. A method according to claim 13, wherein said components include a counterelectrode, the method including at least partly supporting said counter-electrode with said porous, self-supporting body during assembly of said components.

15. A method according to claim 14, wherein said components include a reference electrode, the method further comprising at least partly supporting said reference electrode with said porous, self-supporting body during assembly of the components.

* * * * *